United States Patent [19]
Bürkle et al.

[11] Patent Number: 5,952,169
[45] Date of Patent: Sep. 14, 1999

[54] IDENTIFICATION OF DNA-DAMAGING SUBSTANCES BY MEANS OF CELL LINES CAPABLE OF OVEREXPRESSING POLY (ADP-RIBOSE)—POLYMERASE

[75] Inventors: Alexander Bürkle, Leimen; Léon Van Gool, Heidelberg; Jan-Heiner Küpper, Mauer; Harald Zur Hausen, Hirschberg, all of Germany

[73] Assignee: Deutsches Krebsforschungzentrum Stiftung des Offentlichen Rechts Im Neuenheimer Feld 280, Germany

[21] Appl. No.: 08/649,611

[22] PCT Filed: Sep. 15, 1995

[86] PCT No.: PCT/DE95/01290

§ 371 Date: Jul. 24, 1996

§ 102(e) Date: Jul. 24, 1996

[87] PCT Pub. No.: WO96/08571

PCT Pub. Date: Mar. 21, 1996

[30] Foreign Application Priority Data

Sep. 16, 1994 [DE] Germany ............... 44 33 130

[51] Int. Cl.$^6$ .............. C12Q 1/68; C12Q 1/02; C12N 5/10; C07H 21/04
[52] U.S. Cl. .............. 435/6; 435/7.1; 435/29; 435/40.5; 435/320.1; 435/325; 435/352; 435/455; 536/23.5
[58] Field of Search ............... 435/69.1, 172.1, 435/172.3, 320.1, 325, 352, 368, 6, 7.1, 7.92, 7.4, 29, 40.5; 536/23.1, 23.5

[56] References Cited

PUBLICATIONS

Alkhatib et al., 1987 " Cloning and Expression of cDNA For Human Poly(ADP–Ribose) Polymerase,"*Proc. Natl. Acad. Sci. U.S.A.* 84:1224–1228.

Bhatia et al., 1990, "Expression of The Poly(ADP–Ribose) Polymerase Gene Following Natural And Induced DNA Strand Breakage And Effect of Hyperexpression On DNA Repair," *Carcinogenesis 1*:123–128.

Bürkle et al., 1992, "Poly(ADP–Ribosyl)atiobin: Its Role In Inducible DNA Amplification, And Its Correlation With The Longevity of Mammalian Species," *Exp. Clin. Immunogenet.* 9:230–240.

Cherney et al., 1987, "cDNA Sequence, Protein Structure And Chromosonal Location Of The Human Gene For Poly-(ADP–Ribose)Polymerase," *Proc. Natl. Acad. Sci. U.S.A.* 84:8370–8374.

Fritz et al., 1994, "Effects of Transfection Of Human Poly-(ADP–Ribose) Polymerase In Chinses Hamster Cells On Mutagen Resistance," *Mutation Research 308*:127–133.

Kawamitsu et al., 1984, "Monoclonal Antibodies to Poly-(adenosine diphosphate ribose) Recognize Different Structures," *Biochemistry 23*:3771.

Lavi, 1981, "Carcinogen–mediated Amplification of Viral DNA Sequences in Simian Virus 40–Transformed Chinese Hamster Embryo Cells," *PNAS 78*:6144.

Suzuki et al., 1987, "Molecular Cloning of cDNA For Human Poly(ADP–Ribose) Polymerase and Expression Of Its Gene During HL–60 Cell Differentiation," *Biochem. Biophys. Res. Commun. 146*:403–409.

Uchida et al., 1987, "Nucleotide Sequence Of A Full–Length cDNA For Human Fibroblast Poly(ADP–Ribose) Polymerase," *Biochem. Biophys. Res. Commun. 148*:617–622.

*Primary Examiner*—David Guzo
*Attorney, Agent, or Firm*—Pennie & Edmonds, LLP

[57] ABSTRACT

The present invention relates to a DNA construct containing a cDNA sequence for human poly(ADP-ribose)-polymerase, cell lines containing the DNA construct, and a process for identifying DNA-damaging substances by means of these cell lines which overexpress poly(ADP-ribose)-polymerase.

17 Claims, 2 Drawing Sheets

IDENTIFICATION OF DNA-DAMAGING SUBSTANCES BY MEANS OF CELL LINES CAPABLE OF OVEREXPRESSING POLY (ADP-RIBOSE)— POLYMERASE

TABLE OF CONTENTS
I. FIELD OF THE INVENTION
II. BACKGROUND OF THE INVENTION
III. SUMMARY OF THE INVENTION
IV. BRIEF DESCRIPTION OF THE DRAWINGS
V. BRIEF DESCRIPTION OF THE INVENTION
VI. EXAMPLE
WHAT IS CLAIMED:
ABSTRACT

I. FIELD OF THE INVENTION

The present invention relates to a DNA construct containing a cDNA sequence for human poly(ADP-ribose)-polymerase, cell lines containing the DNA construct and a process for identifying DNA damaging substances by means of these cell lines which overexpress poly(ADP-ribose)-polymerase.

II. BACKGROUND OF THE INVENTION

So far, DNA-damaging substances (physical and chemical carcinogens) which cause the breakage of DNA strands have been identified by measuring the strand breakage either in cell lysates by alkaline DNA denaturation methods (e.g., "alkaline elution") or in situ by means of individual cells (what is called "comet assay"). However, the lysate tests included the drawback that they were technically relatively complicated and required the experimenter's great manual skill. In "comet assays" the reading is also carried out by means of a microscope, which calls for the employment of a complicated apparatus.

Therefore, the object underlying the present invention is to provide a process for rapidly and reliably identifying chemical carcinogens.

III. SUMMARY OF THE INVENTION

The present invention relates to a DNA construct containing a cDNA sequence for human poly(ADP-ribose)-polymerase, cell lines containing the DNA construct, and a process for identifying DNA-damaging substances by means of these cell lines which overexpress poly(ADP-ribose)-polymerase.

IV. BRIEF DESCRIPTION OF THE DRAWINGS

V. BRIEF DESCRIPTION OF THE INVENTION

The principle of the present invention is based on the detection of the cellular poly(ADP-ribose) production as indicator for breakages of DNA strands occurring in living cells. Poly(ADP-ribose) is synthesized by poly(ADP-ribose)-polymerase (PARP) in the presence of DNA strand breakages and by consuming $NAD^+$. This happens under the influence of carcinogenic substances in almost every nucleated cell. However, in such a cell very much poly(ADP-ribose) is formed by manipulation, i.e., by inserting a PARP-DNA sequence in a predetermined combination with a promoter, and can be detected by suitable methods, e.g., immunofluorescence.

Figure 2:
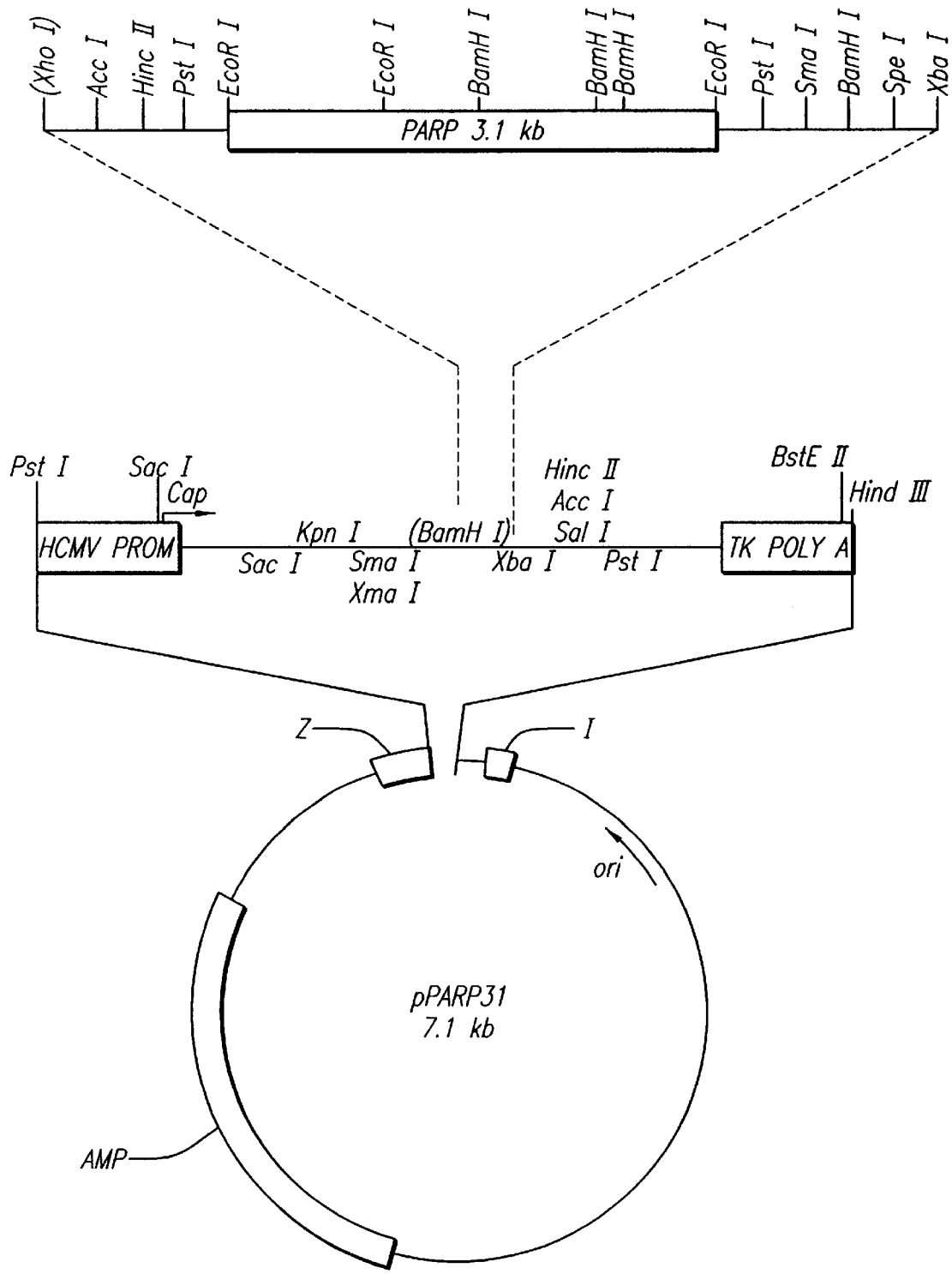
FIG. 2 depicts the cloning diagram for pPARP31.

An example of a construct containing the PARP-DNA sequence is the plasmid pPARP31, deposited with the Deutsche Sammlung von Microorganismen und Zellkulturen (German Type Collection of Microorganisms and Cell Cultures) (DSMZ) at Mascheroder Weg 1b, D-38124 Braunschweig, Germany, under DSMZ Accession Number DSM 12290 on Jun. 29, 1998.

pPARP31 can be obtained by the following steps:

a) Ligating of a cDNA which contains the full open reading frame of poly(ADP-ribose)-polymerase from human embryonal fibroblasts (HEF cells) into pBluescript, thereby obtaining the plasmid pPARP25 (Küpper, doctoral thesis, University of Heidelberg, 1990). The full open reading frame of one of the known PARP-cDNAs is published in the colony bank/EMBL data bank, access number J 03473 (Kurosaki), for example.

b) Isolation of the Xho/Xba fragment from pPARP25.

c) Preparation of the eukaryotic expression vector pL15TK. First, the 650 bp HincII/AvaII fragment of the human cytomegalovirus-promoter/enhancer (HCMV Prom) which has blunt ends, is ligated into the blunt EcoRI site of pUC19 so as to obtain the "intermediate vector" pL15. Then, the 629 bp SmaI/HindIII fragment of the poly-adenylation signal of the herpes simplex virus thymidine kinase gene (TK poly A) is ligated into the blunt SphI site and the HindIII site of pL15 so as to obtain the vector pL15TK. The vector pL15TK contains the resistance gene for ampicillin (Amp), a bacterial replication origin (ori), as well as portions of the Lac operon (Z and I). The polylinker cassette of pUC19 is intact except for the EcoRI and SphI sites.

d) Ligating of the Xho/Xba fragment from pPARP25 into the vector pL15TK (as shown in FIG. 2), thereby obtaining the plasmid pPARP31 (see FIG. 3), the XhoI site of the insert and the BamHI site of the vector being destroyed. The XbaI sites of vector and insert remain intact.

For the production of cell lines, the embryonal hamster cell line CO60 (Lavi, 1981 *PNAS* 78:6144) is stably transfected with a plasmid expressing a poly(ADP-ribose)-polymerase, preferably pPARP31. The resulting cell clones (when pPARP31 was used, these cell clones were referred to as COCF1, −2, −4) overexpress the human PARP. With equal genetically toxic treatment (e.g., gamma-radiation or influence of carcinogenic chemicals), these clones produce markedly more poly(ADP-ribose) than control clones isolated in parallel therewith (COCFN1, −2, −4) which do not show an explosion of human PARP. Similar PARP-overexpressing cell lines can, of course, also be produced from other known base cell lines in addition to the hamster cell line used. Furthermore, PARP-overexpressing cell lines can also be obtained after transient transfection with a PARP-expressing plasmid.

The hamster cell clones COCF1, COCF2, and COCF4 as well as the control cell line COCFN1 were deposited with the DSM under numbers ACC2186, ACC2187, ACC2188 and ACC2189, respectively, on Sep. 6, 1994.

The use of the COCF clones and clones similar thereto, respectively, from other cell lines as indicator cells markedly increases the susceptibility of a detection technique of carcinogens producing breakages of DNA strands. The cellular synthesis of poly(ADP-ribose) leads more or less to a signal amplification, since an individual DNA strand breakage results in the synthesis of several or even many polymer molecules which have up to 200 monomeric elements and thus achieve a considerable complexity. The polymer synthesis is further increased by the transfection of the expression construct containing the PARP sequence, preferably pPARP31. In addition, it is possible to further increase the susceptibility of the detection technique by subjecting the cells to a defined heat shock shortly before the test substance exerts its influence, e.g., 45° C. for thirty (30) minutes, thus inhibiting the decomposition of poly(ADP-ribose) which can compete with the synthesis. The cellularly formed poly(ADP-ribose) is detected preferably in an immunological manner. This includes the advantage that the steps can be carried out easily and the method can be carried out rapidly and takes a few hours. Preferably, the test is conducted by means of fluorescence spectroscopy or on microtiter trays where the specific antibody binding can be evaluated within the meaning of an ELISA by automated measurement. However, all of the other common immunological detection methods, such as immunocytochemistry or immunodotblot, are also suitable. In the latter method, the cells are lysed after treatment with the DNA-damaging test substance, the lysates are applied onto a carrier, e.g., a filter membrane, and the poly(ADP-ribose) formed is detected by means of a poly(ADP-ribose)-specific antibody which may be enzyme-labeled. On the other hand, the above antibody can be unlabeled. The detection is then effected by a second antibody which is directed against the above antibody and is labeled, e.g., enzyme-labeled.

The detection of poly(ADP-ribose) by means of immunofluorescence is to be described by way of example. First, the cells containing the PARP-DNA construct are allowed to grow on, e.g., cover glasses or microtiter trays to common cell density. Then, the cells are treated with a DNA-damaging test substance. The treating period differs for individual test substances. It can easily be determined by a person skilled in the art. Frequently, the treating period is one (1) to fifteen (15) minutes. Thereafter, the cells are fixed to the carrier (e.g., cover glass or microtiter tray). Having washed the carrier, shortly dried and rehydrated the cells in buffer, incubation is carried out with a first antibody against poly(ADP-ribose). After repeated washing, the fluorescence-microscopic evaluation or the detection in an ELISA reader takes place.

For example, gamma-radiation, drugs such as cytostatic agents, U.V. light, food additives or chemicals such as dyes, pigments or coloring substances, solvents or cleaning agents are suitable as DNA-damaging test substance.

The described principle of PARP overexpression can also readily be extended to primary cells from experimental animals in that the expression cassette for human PARP is introduced transiently or stably by means of a viral vector into such primary cell cultures. As a result, cells are available which have the full, tissue-specific foreign matter metabolization capacity. On the one hand, this permits the detection of agents which damage the DNA only after the metabolization, on the other hand, an organospecific damage potential can be assessed by such cells.

Figure 1:
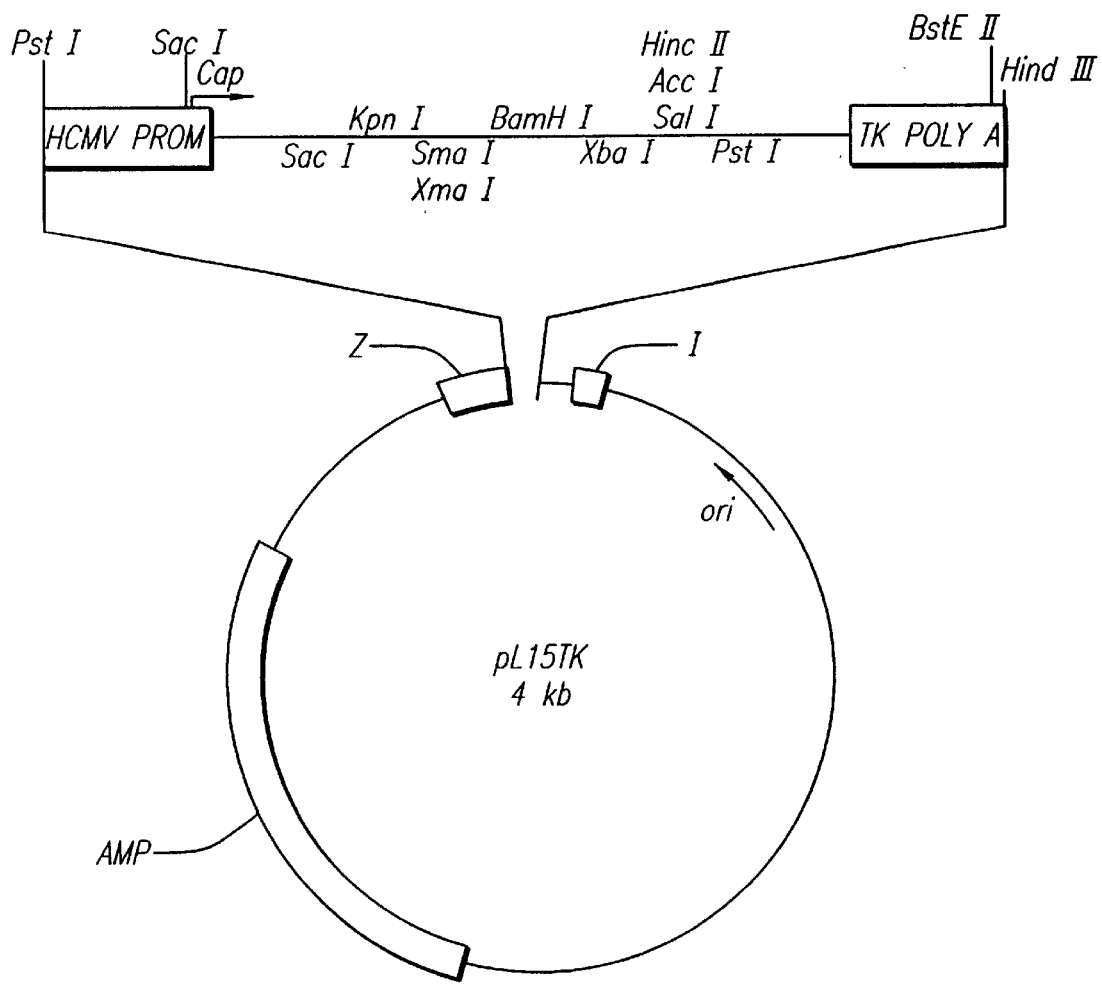
FIG. 1 depicts the eukaryotic expression vector pL15TK.
Figure 3:
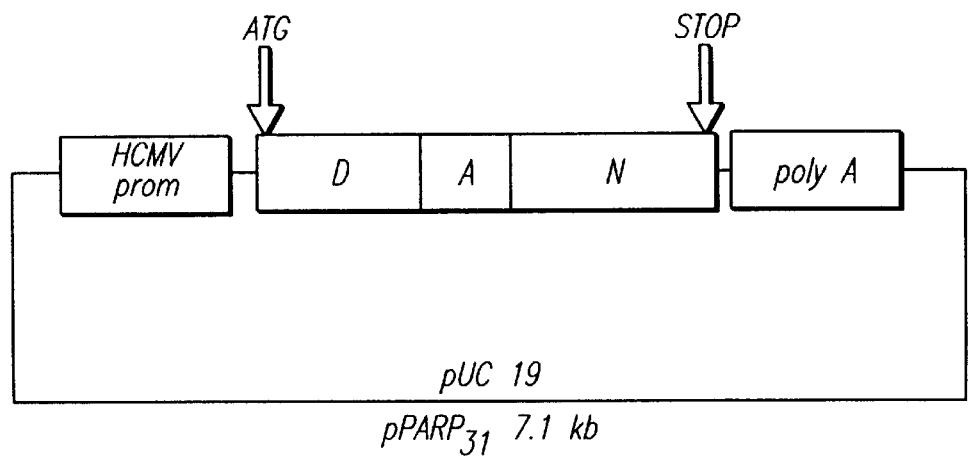
FIG. 3 depicts the genetic map of the plasmid pPARP31.

The invention is further described by means of the FIGURES. More specifically, FIGS. 1, 2 and 3, show the eukaryotic expression vector pL15TK, the cloning diagram for pPARP31, and the genetic map of the plasmid pPARP31, respectively.

The abbreviations in the FIGURES have the following meanings:

HCMV Prom: human cytomegalovirus-promoter/enhancer
AMP: ampicillin resistance gene
Z: portion of the Lac operon
I: portion of the Lac operon
(TK)Poly A: polyadenylation signal of the herpes simplex virus thymidine kinase gene
ori: bacterial replication origin
D: DNA binding domain
A: automodification domain
N: NAD binding domain
ATG: initiation codon
Stop: stop codon.

The common abbreviations were used for the restriction sites.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLE

COCF1 cells were cultivated on cover glasses overnight. The cells were treated with 2.8–20 Gray gamma-radiation. Five minutes after the radiation onset, the cells were fixed in 10% trichloroacetic acid (ten (10) minutes on ice). The clover glasses were washed in 70%, 90% and absolute ethanol for three (3) minutes each. After air-drying for one (1) minute, the cells were rehydrated in PBS buffer (phosphate-buffered salt solution) for one (1) minute. The first antibody was added (cell culture supernatant of the hybridoma 10H (described by Kawamitsu et al., 1984, *Biochemistry* 23:3771) which secretes a monoclonal, highly specific antibody against poly(ADP-ribose)). Then, the cover glasses were washed three times in PBS buffer for five (5) minutes and the second antibody (FITC-coupled goat-anti-mouse-immunoglobulins; Renner company, Dannstadt) was added and incubated at 37° C. for thirty (30) minutes. Thereafter, the cover glasses were washed again three times with PBS buffer for five (5) minutes and embedded in polyvinyl alcohol on slides. The evaluation was made by means of fluorescence microscopy.

What is claimed:

1. Plasmid pPARP31, which was deposited with the Deutsche Sammlung von Microorganismen und Zellkulturen (German Type Collection of Microorganisms and Cell Cultures) (DSMZ) under DSMZ Accession Number DSM 12290.

2. A cell line which stably overexpresses poly(ADP-ribose)-polymerase and thereby induces an enhanced accumulation of poly(ADP-ribose), comprising a DNA construct having a nucleic acid sequence for human PARP.

3. The cell line according to claim 2, wherein the nucleic acid sequence is a cDNA sequence.

4. The cell line according to claim 3, wherein the DNA construct is pPARP31, which was deposited with the Deutsche Sammlung von Microorganismen und Zellkulturen (German Type Collection of Microorganisms and Cell Cultures) (DSMZ) under DSMZ Accession Number DSM 12290.

5. The cell line according to claim 4, wherein the cell line is the hamster cell line CO60.

6. The cell line according to claim 5, wherein the cell line is a cell clone selected from the group consisting of COCF1, COCF2, and COCFR4.

7. A process for identifying a DNA-damaging substance, comprising:
   (a) exposing cells which overexpress poly(ADP-ribose) in response to DNA damage to a test substance; and
   (b) identifying a DNA-damaging substance by determining immunologically whether said cells overexpress poly(ADP-ribose).

8. The process according to claim 7, wherein the cells are selected from the group consisting of the cell clones COCF-1, COCF-2, COCF-4.

9. The process according to claim 7, wherein the cells are grown on a carrier.

10. The process according to claim 8, wherein the cells are grown on a carrier.

11. The process according to claim 9, wherein the carrier is selected from the group consisting of a cover glass and a microtiter tray.

12. A process for identifying a DNA-damaging substance, comprising:
   (a) exposing cells which overexpress poly(ADP-ribose) in response to DNA damage to a test substance;
   (b) lysing said cells to generate a lysate; and
   (c) identifying a DNA-damaging substance by detecting immunologically whether said lysate comprises poly(ADP-ribose).

13. The process according to claim 12, wherein the cells are selected from the group consisting of the cell clones COCF-1, COCF-2, and COCF-4.

14. The process according to claim 12 or 13, wherein the lysates are applied to a carrier prior to said identifying.

15. The process according to claim 14, wherein the carrier is a filter membrane.

16. The process according to claim 10, wherein the carrier is selected from the group consisting of a cover glass and a microtiter tray.

17. The process according to any one of claims 7, 8, 9, 11, 10, or 16, wherein the immunological detection is carried out via fluorescence microscopy.

* * * * *